Figure 1:
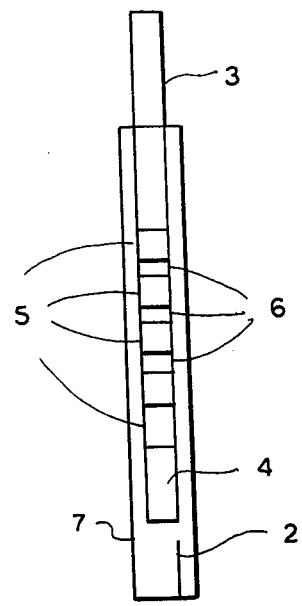

| United States Patent [19] | [11] | 4,252,903 |
|---|---|---|
| Kallies | [45] | Feb. 24, 1981 |

[54] INDICATOR-CAPILLARY FOR UREA-DETERMINATION

[76] Inventor: Karl-Heinz Kallies, Sebnitz, German Democratic Rep.

[21] Appl. No.: 957,358

[22] Filed: Nov. 3, 1978

[30] Foreign Application Priority Data

Nov. 4, 1977 [DD] German Democratic Rep. ... 201873

[51] Int. Cl.$^3$ ............................................... C12M 1/28
[52] U.S. Cl. ..................................... 435/294; 435/12;
435/805; 435/810; 435/296; 422/56; 422/61
[58] Field of Search .......... 435/12, 805, 810, 292–294,
435/296; 422/56, 55, 61; 23/230 B

[56] References Cited

U.S. PATENT DOCUMENTS

| 3,249,513 | 5/1966 | Babson | 435/12 |
| 3,873,269 | 3/1975 | Kraffczyk et al. | 435/12 |
| 3,884,641 | 5/1975 | Kraffczyk et al. | 435/12 |
| 3,950,226 | 4/1976 | Chang | 435/12 |
| 4,066,403 | 1/1978 | Bruschi | 435/12 |
| 4,094,647 | 6/1978 | Deutsch et al. | 435/805 |

Primary Examiner—Benoit Castel
Attorney, Agent, or Firm—Michael J. Striker

[57] ABSTRACT

An indicator for urea determination has a capillary tube provided on the inside with an indicator-signal band in form of stripe-shaped signal zones treated with a dyestuff which changes color in the alkaline range; there are untreated spaces between the stripe-shaped signal zones. The lower end of the capillary tube has a colored mark to indicate the level to which it is to be filled.

8 Claims, 3 Drawing Figures

INDICATOR-CAPILLARY FOR UREA-DETERMINATION

The invention concerns an indicator-capillary for urea-determination.

The enzymatic reaction of urea with urease, which leads to the formation of ammonia and carbon dioxide, has previously been described for a quick-test.

It is measured through the pH change and coloring of appropriate indicators following ammonia production. The determination ensues either in the urease-zone directly simultaneously through an introduced pH-indicator (DE-AS 1 498 601 and DE-AS 1 598 756) or on a separated from the urease-zone applied indicator after liberation of the ammonia as a gas (DE-AS 1 245 619 and DE-AS 2 249 647).

Through known additives the sensitivity of the reaction and the color stability are improved, respectively through an alkaline buffering under addition of organic acids and stabilizing substances the reaction capability and storage capacity are achieved.

The calibration of the indicator zone is achieved with organic acids.

Increasingly the urea determination in whole blood is taken in rescue service, at the sick bed or as serum in ambulances. The previously described and prepared stripes require for an accurate declaration, that is quantitative determinations respectively half-quantitative determinations, an accurate pipetting between 0.01 and 0.1 ml. The stripes must, in order that they can be used for a longer time, be kept in a refrigerator and are sensitive to basic components in the air.

The evaluation requires aids for the measurement, which are either printed or a stencil is used. The indicator-zone is colored with a transition range, which is indistinctly indicated from blue to green. The determination of the borderline as well as the thus-created meniscus makes the unpracticed unsure in the determination.

The production of separated stripes with so many different reagent additives is complicated. In order to obtain a good reproducibility of the production batches, a very careful working and standardizing is necessary.

As the urease activity is already inhibited by traces of unknown metals, high purity furtherances must be placed on the chemicals.

It is therefore the goal of the invention to develop an indicator-capillary that can serve for the taking of a measured blood- or serum-amount from the body and for the content measurement of urea in the taken blood or serum and which requires no further helping aids.

The task of the invention lies in this, to prepare a marked capillary tube with an indicator-signal-band in order, that the possibility of taking a known amount of a urea-containing solution is joined with a quick report of high accuracy.

The noted task is solved through the invention in that a capillary tube of glass or plastic serves for the carrying out of the invention.

The capillary tube is provided with a colored mark at the lower end, up to which it is to be filled with blood or serum for the test.

The mark is determined by the to-be-taken liquid measure and is defined by the internal diameter of the capillary tube, the utilized carrier material and the length of the reaction zone of the indicator stripe. Capillary tube with a length from 40 to 120 mm, preferably 60 mm, can with a constant interior diameter from 1 to 3 mm, preferably 2.5 mm, be prepared. But it can also exhibit above the marking an enlarged reaction room through the portionwise enlargement of the interior diameter up to 10 mm.

In the interior of the capillary-tube an indicator signalband is located, on which beyond the reaction zone one or more indicator-solutions as signal zones in stripes next to each other with a width of from 1 to 5 mm, preferably 2 mm, is applied. Spaces from 1 to 10 mm between the indicator-signal zones remain, untreated.

The indicator-signalbands for the capillary tube can be prepared from different carrier materials of natural or synthetic fibers, previously determining that the carrier material has no effect on the reaction and is sufficiently absorbent.

Preferably, filter paper with a weight from 60 to 400 $g/m^2$ is used. The division of the indicator-signalband into reaction-zones and indicator-signal-zones is determined by the paper size and the applied enzyme activity.

Through the use of a capillary tube a sufficient measurement, for example from 10 to 30 $\mu l$ serum or blood, even by unpracticed workers or lay persons is possible. The determination can be performed at the sick bed with the capillary tube and without other aids. External influences, for example through alkaline air on the indicator, are possible only under extreme circumstances due to the protection in the capillary tube.

The capillary tube makes for constant reaction conditions, which lead to a controlled gas-evolution and diffusion.

As the gas evolution does not run linearly with the urea concentration, the indicator zones are either so prepared that they correspond to the evolution, or each zone is either so prepared through the use of another suitable indicator or the addition of an organic acid, that this condition is taken into account. The reaction runs so, that already [immediately] the lowest level in the physiological range is reached and thus there is always given a control for the effectiveness of the capillary tube and the indicator signalband.

Through the separation of the indicator-zone into signal zones of different stripes the evaluation by unpracticed workers is improved.

A marking of the indicator-signalzone with different, alternately applied indicators gives a better color contrast, simplifies the evaluation and makes it more precise.

The indicator stripes are furthermore to be characterized in that the urease preparation to be found in the reaction zone for urea determination contains an addition of saccharides or polysaccharides from 1 to 15%, preferably glucose.

Urease-preparations that are not highly purified, upon application on an absorbent carrier, tend to be hydrophobic, so that the reaction zone cannot absorb the blood or serum fast enough. The addition of saccharides or polysaccharides eliminates this inconvenience and effects simultaneously the stability of the enzyme activity during storage under normal conditions in a stabilizing manner. Storage in a refrigerator can be eliminated.

The indicator stripes are also to be characterized in that the reaction zone contains no buffer, no addition of alkali carbonate and/or alkali hydroxide and a slightly purified urease.

Thereby a shortening of the reaction time can be achieved without reduction in the accuracy.

The indicator stripes are to be characterized in that the indicator zones contain as additive indicators a dyestuff which changes in the alkaline range, preferably the dyestuff Brilliant-yellow.

The evaluation is simplified and improved through an additive indicator which has another color change. The dyestuff Brilliant-yellow is colored red through the produced $NH_3$-gas.

EXPLANATORY EXAMPLES

Figure 2:
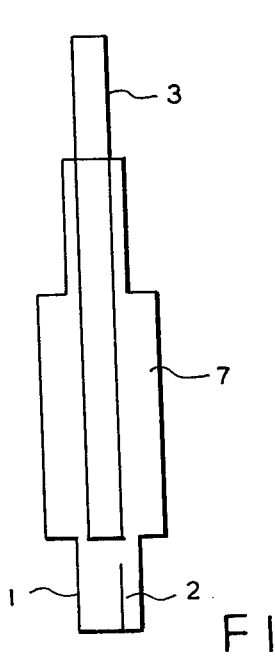
Figure 3:
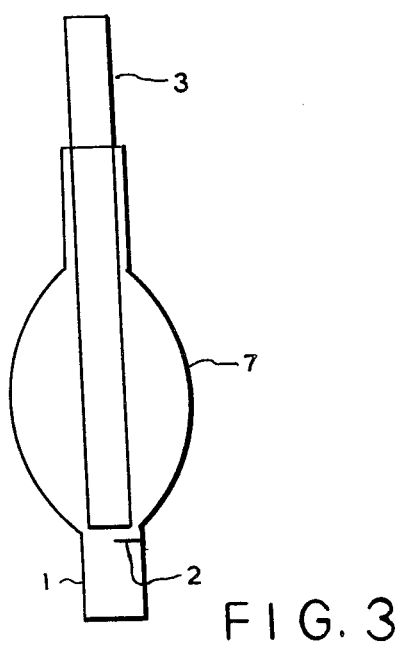

The invention shall be further explained in a few explanatory examples. In the appended drawing there is shown in:

FIG. 1: an indicator-capillary with constant internal diameter of the capillary tube, FIGS. 2, 3: an indicator-capillary with a partially enlarged internal diameter of the capillary tube.

EXAMPLE 1

For the capillary tube illustrated in FIG. 1 there is chosen a capillary of plastic with an internal diameter of 2.5 mm and a length of 60 mm, which has a marking 2 at 4 mm. For the indicator-signalband 3 a filter cardboard with a surface weight of 200 g/m$^2$ is chosen.

The reaction zone 4 is impregnated as follows:
Urease corresponding to 4,500 IE
Glucose as additive: 1 g
Distilled water: 10 ml.
A 20 mm wide edge of the filter cardboard is immersed in this solution. Simultaneously and adjacent to this reaction system 4 a 4 mm wide stripe of a 20% solution of stearic acid in carbon tetrachloride is applied. This hydrophobic zone hinders the adsorption of the liquid to be examined into the indicator signal zones 5. It can also be produced with known hydrophobic agents for textiles or paper and range in its width between 2 and 5 mm. Simultaneously with the urease solution and the hydrophobic solution the indicator-signalbands 5 above the hydrophobic zone are applied according to examples 2 to 4. Their arrangement is determined by whether a half-quantitative or a quantitative determination is to be carried out.

The thus-prepared filter cardboard is cut into narrow indicator signalbands. In each case one indicator-signalband 3 is placed within a capillary tube 1. Should a test for urea follow, the indicator signalband 3 is raised about 10 mm above the marking 2. The marked end of the capillary tube 1 is dipped into the liquid to be tested. Were the filling inadvertently to follow over the marking 2, with a filter paper strip the excess liquid is adsorbed and thus easily and accurately adjusted.

Through a return-pushing of the indicator signalband 3 to the marking 2 the determination is begun.

The reaction is carried out at 25° C. and evaluated after 15 minutes.

EXAMPLE 2

Brilliant-yellow: 10 mg
Ethanol: 10 ml
The indicator solution is so applied in 2 to 3 mm wide stripes above the hydrophobic zone that always a 1 to 2 mm wide space remains between. With this indicator signalband 3, which contains five indicator signalzones 5, the determination in the capillary 1 described in Example 1 with blood or serum at 25° C. is carried out and after 15 minutes the evaluation made.

A first evaluation of higher concentration can follow after 5 minutes. Each indicator signalzone 5 corresponds, according to the selected width and the selected space between, to a known amount of urea. The values thereto are read off a table given therewith, or can be printed on the stripes.

EXAMPLE 3

A capillary according to Example 1 is used as capillary tube 1.
Solution (a)
Bromocresol green: 40 mg
tartaric acid: 100 mg
ethanol: 10 ml
Solution (b)
Brilliant-yellow: 40 mg
ethanol: 10 ml
The so-prepared indicator-solutions are applied above the hydrophobic zone in the following arrangement:
1. Indicator-signalzone solution (a) 2 to 3 mm wide
Space between 1 mm
2. Indicator-signalzone solution (b) 2 to 3 mm wide
Space between 1 mm
3. Indicator-signalzone solution (a) 2 to 3 mm wide
Space between 2 mm
4. Indicator-signalzone solution (a) 2 to 3 mm wide
Space between 3 mm
5. Indicator-signalzone solution (a) 2 to 3 mm wide
The values corresponding are given on the capillary 1 or on the indicator-signalband 3 respectively.

The use of an indicator which turns red for the second indicator-signalzone should signal the beginning of heightened urea-nitrogen-values.

The reaction is carried out at 25° C. and evaluated after 15 minutes.

EXAMPLE 4

Bromocresol green: 30 mg
Tartaric acid: 60 mg
Ethanol: 10 ml
The indicator-solution prepared in a known manner is applied in signalzones 5 from 1 to 3 mm wide in different intervals above the hydrophobic zone. The spaces 6 and the number of indicator-signalzones 5 determine the accuracy and the measurable amounts.

When between the 1st and 2nd signalzone an interval of 1 mm, between the 2nd and 3rd an interval of 2 mm and between the 3rd and 4th an interval of 4 mm are established, the 1st signalzone corresponds to a reading of 20 mg urea/nitrogen. The second signalzone shows 30 mg urea/nitrogen, the 3rd signalzone 45 mg urea/nitrogen and the 4th signalzone 60 mg urea/nitrogen.

Used in accordance with FIG. 2 is a capillary with widened reaction room 7, which in the range of the marking is 10 mm long and has an internal diameter of 2.5 mm. Thereon is joined a 30 mm long, broadened portion with an internal diameter of 7 mm and follows a 20 mm long portion of capillary with a 2.5 mm internal diameter.

The reaction time is shortened to 7 minutes.

I claim:

1. An indicator capillary for urea determination, comprising a capillary tube of glass or plastic having an internal diameter of from about 1 to 3 mm and a length of from about 40 to 120 mm; an indicator signal-band of natural or synthetic fibers inside said capillary tube, said indicator signal-band containing an unbuffered, alkali-carbonate and alkali-hydroxide-free reaction system of slightly purified urease and about 1 to 15% of a saccharide or polysaccharide, said indicator signalband having one or more stripe-shaped indicator signal zones treated with a dyestuff indicator which changes color in the alkaline range and also having untreated spaces between said signal zones; and a colored mark on a lower end portion of the capillary tube to indicate the intended filling level of the tube.

2. The indicator-capillary of claim 1, further comprising an enlarged reaction room inside said capillary tube with an interior diameter up to about 10 mm.

3. The indicator-capillary of claim 1, wherein said capillary tube has an internal diameter of about 2.5 mm and a length of about 60 mm.

4. The indicator-capillary of claim 1, wherein said indicator signalband is made from filter paper of a weight from about 60 to 400 g/m$^2$.

5. The indicator-capillary of claim 1, wherein said saccharide is glucose.

6. The indicator-capillary of claim 1, wherein said dyestuff indicator is brilliant yellow.

7. The indicator capillary of claim 1, wherein said stripe-shaped indicator signal zones have a width of from about 1 to 5 mm and the untreated spaces have a width of from about 1 to 10 mm.

8. The indicator-capillary of claim 7, wherein said stripe-shaped indicator signalzones have a width of about 2 mm.

* * * * *